Figure 1:
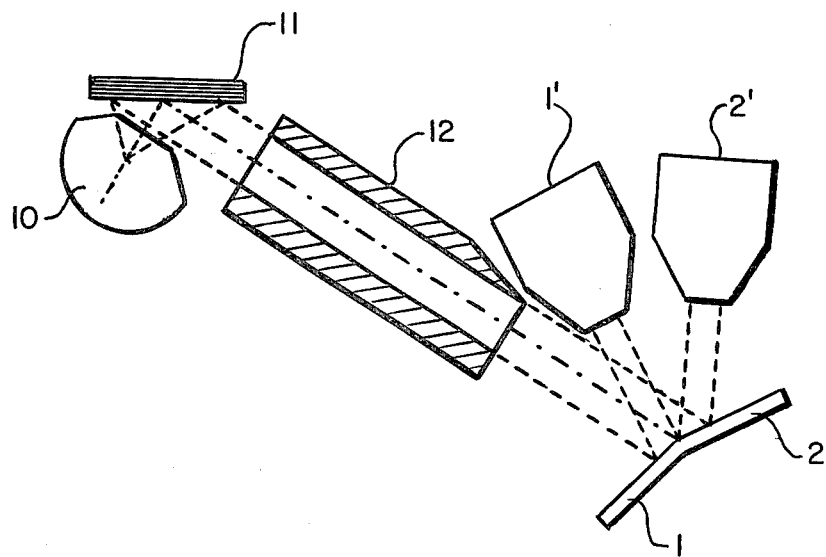

United States Patent [19]

Jenkins

[11] Patent Number: 4,472,825
[45] Date of Patent: Sep. 18, 1984

[54] DOUBLE CRYSTAL X-RAY SPECTROMETER

[75] Inventor: Ronald Jenkins, Peekskill, N.Y.

[73] Assignee: U.S. Philips Corporation, New York, N.Y.

[21] Appl. No.: 382,015

[22] Filed: May 26, 1982

[51] Int. Cl.³ ............................................. G01N 23/22
[52] U.S. Cl. ........................................ 378/49; 378/83; 378/85
[58] Field of Search .................. 378/45, 46, 47, 48, 378/49, 83, 84, 85

[56] References Cited

U.S. PATENT DOCUMENTS 3,060,314 10/1962 Wytzes ................................. 378/49
3,397,312 8/1968 Okano .................................. 378/49
3,980,568 9/1976 Pitchford ............................. 378/49

Primary Examiner—Craig E. Church
Attorney, Agent, or Firm—Paul R. Miller

[57] ABSTRACT

A two crystal detection system is provided for the measurement of X-ray spectra in which two half crystals are arranged at a fixed angular difference and each crystal is read out by a separate gas detector. In such a structure, both short "d" and long "d" spacings may be simultaneously measured. This construction of the present invention yields two integrated scanning channels in which both wavelength spectra can simultaneously be achieved.

9 Claims, 3 Drawing Figures

U.S. Patent  Sep. 18, 1984  Sheet 1 of 2  4,472,825

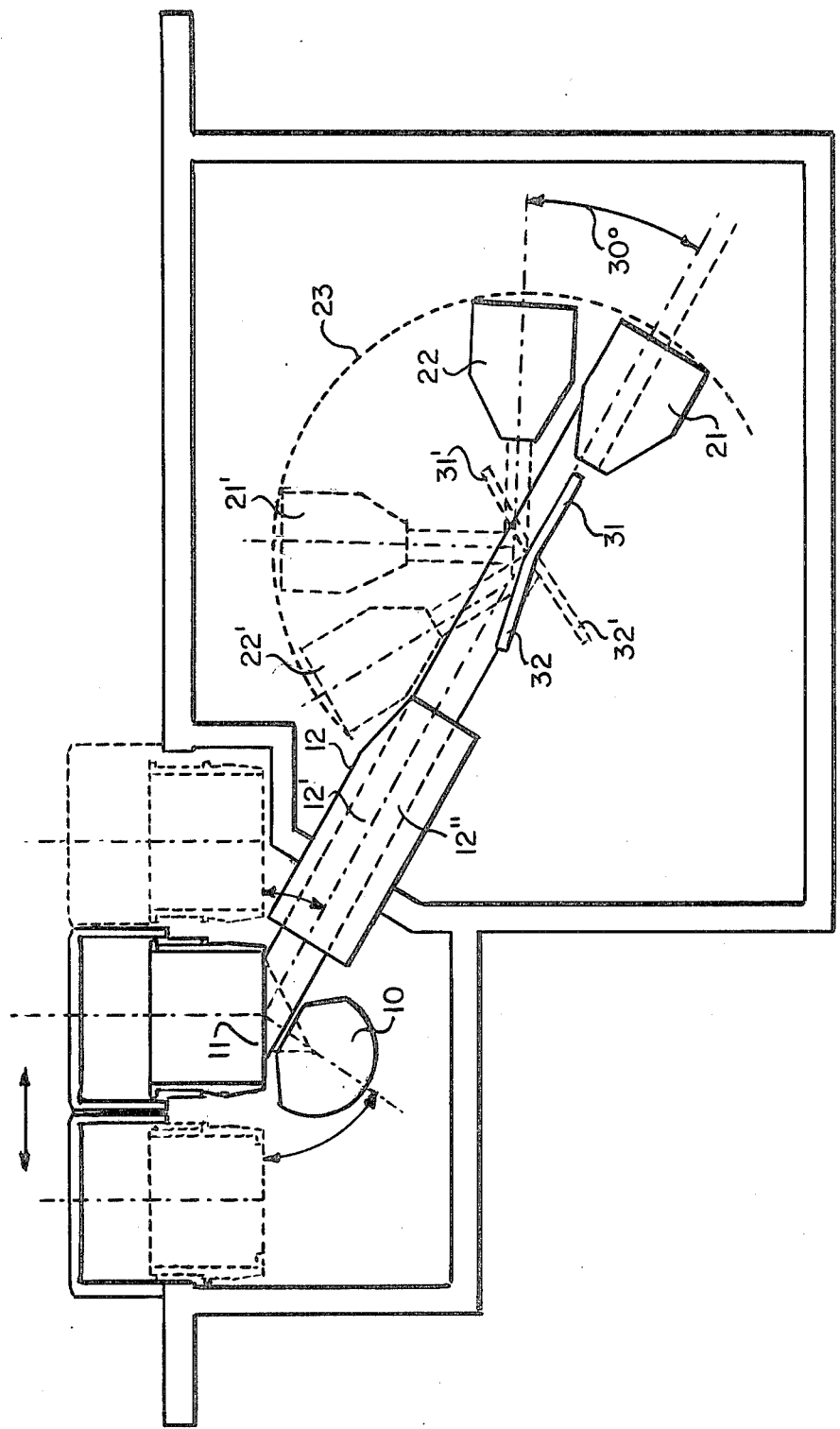

DOUBLE CRYSTAL X-RAY SPECTROMETER

The present invention involves an improved X-ray spectrometer structure utilizing two crystals and corresponding detectors in order to acquire simultaneous long and short wavelength spectra.

X-ray spectrometers which have existed in the prior art include an X-ray tube providing X-rays on a specimen. Characteristic X-ray photons are excited from the specimen and directed through a parallel plate collimator onto a crystal which diffracts the X-rays to a detector. The structure of the spectrometer usually involves a single detector channel with a single crystal for diffracting X-rays to a single gas detector to obtain an electrical readout of the sample information. A principal difficulty with this prior art spectrometer is that the single collimator-detector-crystal combination must be replaced for obtaining measurements for each different wavelength range.

The present invention provides an arrangement for obtaining measurements over a wide range of different wavelengths without making changes in the collimator-detector structure.

The basis of the present invention involves the use of two "half" crystals arranged at a fixed angular difference with two detectors coupled individually to the two half crystals so that two integrated scanning channels are obtained in which long and short wavelength spectra can simultaneously be acquired. This structure of the present invention utilizes a collimator in which the usual collimator structure is replaced by arranging half of the blades at a larger spacing than the other half. In this manner, the X-rays from the sample can be simultaneously exposed into two separate dispersion channels onto two different crystals with two separate detection counters reading out information from these two crystals.

Figure 3:
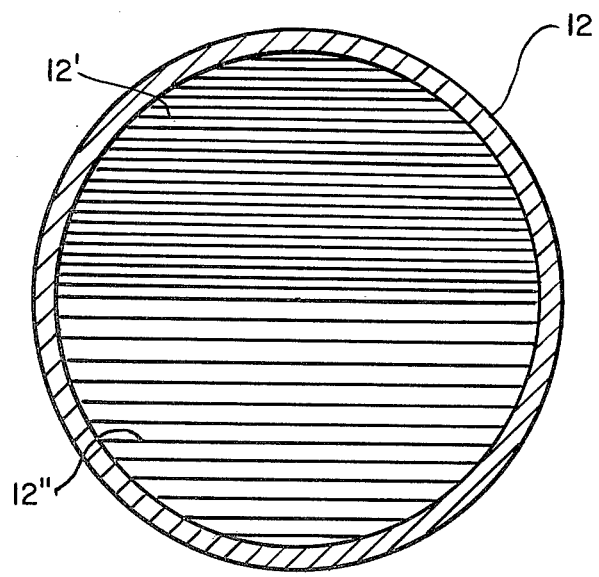

The structure of the present invention may be more clearly seen by reference to the drawings figures which illustrate various aspects and embodiments of the present invention without limitation, and wherein FIG. 1 illustrates a partial arrangement of the detector system of the present invention, FIG. 2 illustrates in more detail the X-ray spectrometer with the detector arrangement of the present invention in different positions, and FIG. 3 illustrates in cross-section the collimator of the present invention.

The arrangement of the present invention may be seen in FIG. 1, wherein an X-ray tube 10 directs primary X-rays onto a specimen 11 which in turn generates characteristic spectra from the sample through collimator 12 onto the pair of "half" crystals 1 and 2 respectively diffracting to detectors 1' and 2'. The crystals 1 and 2 are mounted edge-on at a surface angle of about 15°. The two detectors 1' and 2' are mounted as a single assembly with detector 1' being aligned with the half crystal 1 and the detector 2' being aligned with the crystal 2.

A goniometer (not illustrated) moves the two crystals and the two detectors in the usual 2:1 relationship to maintain the geometric conditions for two integrated spectrometer channels. The two detectors 1' and 2' typically involve a flow counter detector and a high pressure sealed counter detector with the flow counter being aligned to the longer "d" spacing half crystal and the sealed counter being aligned to the smaller "d" spacing half crystal.

This arrangement of detectors and half crystals is mounted for rotation on the goniometer circle 23 as may be seen in FIG. 2. For example, the respective half crystals 31 and 32 are aligned with the detectors 21 and 22. The detector 21 aligned with the half crystal 31 may be a sealed detector wherein the half crystal 31 receives X-ray spectra through the fine collimated structure 12' of the collimator 12 (FIG. 3). The half crystal 32 receives X-ray spectra through the coarse spacing 12" of the collimator 12 and reflects it to the flow counter detector 22. There is a 30° fixed angle between the detectors 21 and 22, and a corresponding 15° angle between the half crystals 31 and 32.

As may be seen in FIG. 2, the crystals and detectors may be rotated on the goniometer circle so that the detector positions 21' and 22' are arrived at with the two half crystals respectively being at the positions 31' and 32'.

These detectors and crystals may be moved through a number of positions with the angular offset between the detectors being maintained at 30°, and an angular offset between the crystals is maintained at a 15° thereby providing a 2:1 relationship.

The detector 21, for example, relative to the short "d" spacing crystal 31 may be a sealed, high pressure gas detector, with a gas such as xenon. The detector 22 relative to the half crystal 32 for longer "d" spacing may be a gas flow proportional detector. Readout from the detectors is established and maintained through normal electrical and electronic circuitry.

The collimator 12 is seen in cross-section in FIG. 3 and includes two series of blades arranged at different spacings. The blades 12' provide a fine spacing portion, while the blades 12" provides a coarse spacing portion. The blades of the collimator providing the coarse spacing portion 12" may have a spacing of about two and a half to three times the spacing of the blades in the fine spacing portion 12'.

As an example, the portion 12' may have a spacing between blades of about 200 microns, while the portion 12" may have a spacing between blades of about 500 microns. This geometric arrangement provides two separate, but integrated, channels. One channel is formed by the coarse spacing portion 12" in conjunction with crystal 32 and detector 22, while the other channel is formed by the fine spacing portion 12' in conjunction with the crystal 31 and the sealed detector 21. By this collimator structure, two integrated scanning channels having both long and short wavelength spectra can simultaneously be acquired.

The sample 11 may be of a solid or a liquid type sample.

While various arrangements and features of the present invention have been illustrated and described, the present invention includes all modifications and variations which may be evident from the claims.

What I claim:

1. An X-ray spectrometer comprising: an X-ray source, a sample receiving X-rays from said source, collimating means for directing secondary radiation from said sample onto a diffracting crystal, said collimating means including a collimator having two separate blade arrangements with two different spacings, and detector means including two separate respective detectors and two angularly disposed diffraction crystals receiving collimated X-rays through said two different spacings with each of said crystals simultaneously passing diffracted X-ray spectra to said respective detectors.

2. An X-ray spectrometer according to claim 1, wherein said two separate blade arrangements have spacings in one blade arrangement of 2.5 to 3 times the spacings in the second of said two blade arrangements.

3. An X-ray sepctrometer according to claim 1, wherein said respective detectors include a high pressure sealed detector receiving diffracting X-ray spectra from a first "d" spacing, and a flow detector receiving diffracted X-ray spectra from a second larger "d" spacing.

4. An X-ray spectrometer according to claim 1, wherein said two diffraction crystals are angularly maintained at an angle of 15° between one another.

5. An X-ray spectrometer according to claim 1, wherein said separate respective detectors are maintained at a fixed angular relationship with each other.

6. An X-ray spectrometer according to claim 5, wherein said two diffraction crystals are angularly maintained at an angle of 15° between one another.

7. An X-ray spectrometer according to claim 1, wherein said two separate blade arrangements include two sets of parallel blades with each of said sets being parallel to each other.

8. An X-ray spectrometer according to claim 7, wherein one of said two sets has a spacing of about 200 microns between said parallel blades, and the second of said two sets has a spacing of about 500 microns between said parallel blades.

9. An X-ray spectrometer according to claim 7, wherein said two separate blade arrangements have spacings in one blade arrangement of 2.5 to 3 times the spacings in the second of said two blade arrangements.

* * * * *

UNITED STATES PATENT AND TRADEMARK OFFICE
CERTIFICATE OF CORRECTION

PATENT NO. : 4,472,825

DATED : September 18, 1984

INVENTOR(S) : RONALD JENKINS

It is certified that error appears in the above-identified patent and that said Letters Patent is hereby corrected as shown below:

In the Title Page change the assignee from "U.S. PHILIPS CORPORATION" to --NORTH AMERICAN PHILIPS CORPORATION--.

*Signed and Sealed this*

*Fourteenth* Day of *January 1986*

[SEAL]

*Attest:*

*Attesting Officer*

DONALD J. QUIGG

*Commissioner of Patents and Trademarks*